(12) United States Patent  
Desmond, III

(10) Patent No.: US 7,996,976 B2
(45) Date of Patent: Aug. 16, 2011

(54) RETAINING STENT

(75) Inventor: Joseph P. Desmond, III, Bloomington, IN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 431 days.

(21) Appl. No.: 11/625,438

(22) Filed: Jan. 22, 2007

(65) Prior Publication Data

US 2007/0118228 A1    May 24, 2007

Related U.S. Application Data

(63) Continuation of application No. 10/400,201, filed on Mar. 25, 2003, now Pat. No. 7,182,745.

(51) Int. Cl.
*B21D 39/03* (2006.01)
*B23P 11/00* (2006.01)

(52) U.S. Cl. .................. 29/428; 604/8; 604/104
(58) Field of Classification Search .......... 29/428; 604/101.01, 101.02, 101.03, 101.04, 8
See application file for complete search history.

(56) References Cited

U.S. PATENT DOCUMENTS

| | | |
|---|---|---|
| 3,860,006 A | 1/1975 | Patel |
| 3,890,977 A | 6/1975 | Wilson |
| 3,920,023 A | 11/1975 | Dye et al. |
| 4,022,216 A | 5/1977 | Stevens |
| 4,212,304 A | 7/1980 | Finney |
| 4,307,723 A | 12/1981 | Finney |
| 4,334,327 A | 6/1982 | Lyman et al. |
| 4,405,314 A | 9/1983 | Cope |
| 4,419,094 A | 12/1983 | Patel |
| 4,531,933 A | 7/1985 | Norton et al. |
| 4,568,338 A | 2/1986 | Todd |
| 4,610,657 A | 9/1986 | Densow |
| 4,643,716 A | 2/1987 | Drach |
| 4,694,838 A | 9/1987 | Wijayarthna et al. |
| 4,705,502 A | 11/1987 | Patel |
| 4,713,049 A | 12/1987 | Carter |
| 4,738,667 A | 4/1988 | Galloway |
| 4,747,840 A | 5/1988 | Ladika et al. |
| 4,787,884 A | 11/1988 | Goldberg |
| 4,790,809 A | 12/1988 | Kuntz |
| 4,790,810 A | 12/1988 | Pugh, Jr. et al. |
| 4,813,925 A | 3/1989 | Anderson, Jr. et al. |
| 4,820,262 A | 4/1989 | Finney |
| 4,846,814 A | 7/1989 | Ruiz |
| 4,867,742 A | 9/1989 | Calderon |

(Continued)

FOREIGN PATENT DOCUMENTS

EP    0023208    7/1980

(Continued)

OTHER PUBLICATIONS

Bard Urological Division Product Catalog, 1990.

(Continued)

*Primary Examiner* — David P Bryant
*Assistant Examiner* — Christopher M Koehler

(57) ABSTRACT

A medical device for use within a body of a patient includes at least two retention members located at a first end of an elongated section of the medical device. The retention members are adapted to limit longitudinal movement of the elongated section when the medical device is placed within the body of a patient. The elongated section can define a passage and at least one opening in communication with the passage to facilitate passing fluid.

33 Claims, 13 Drawing Sheets

U.S. PATENT DOCUMENTS

| | | | |
|---|---|---|---|
| 4,874,360 A | | 10/1989 | Goldberg et al. |
| 4,887,996 A | | 12/1989 | Bengmark |
| 4,931,037 A | | 6/1990 | Wetterman |
| 4,950,228 A | | 8/1990 | Knapp, Jr. et al. |
| 4,976,692 A | * | 12/1990 | Atad ................... 604/101.03 |
| 4,986,814 A | | 1/1991 | Burney et al. |
| 4,990,133 A | | 2/1991 | Solazzo |
| 5,019,102 A | | 5/1991 | Hoene |
| 5,041,092 A | * | 8/1991 | Barwick ................... 604/104 |
| 5,052,998 A | * | 10/1991 | Zimmon ................... 604/8 |
| 5,116,309 A | | 5/1992 | Coll |
| 5,122,122 A | | 6/1992 | Allgood |
| 5,137,513 A | | 8/1992 | McInnes et al. |
| 5,141,502 A | | 8/1992 | Macaluso, Jr. |
| 5,158,540 A | | 10/1992 | Wijay et al. |
| 5,176,625 A | | 1/1993 | Brisson |
| 5,176,626 A | * | 1/1993 | Soehendra ................... 604/8 |
| 5,221,253 A | | 6/1993 | Coll |
| 5,269,802 A | | 12/1993 | Garber |
| 5,282,784 A | | 2/1994 | Willard |
| 5,295,954 A | | 3/1994 | Sachse |
| 5,306,241 A | | 4/1994 | Samples |
| 5,320,605 A | * | 6/1994 | Sahota ................... 604/101.01 |
| 5,346,467 A | | 9/1994 | Coll |
| 5,354,263 A | | 10/1994 | Coll |
| 5,364,340 A | | 11/1994 | Coll |
| 5,401,257 A | | 3/1995 | Chevalier, Jr. et al. |
| 5,509,900 A | * | 4/1996 | Kirkman ................... 604/104 |
| 5,514,092 A | | 5/1996 | Forman et al. |
| 5,531,741 A | | 7/1996 | Barbacci |
| 5,542,924 A | | 8/1996 | Snoke et al. |
| 5,565,523 A | | 10/1996 | Chen et al. |
| 5,599,291 A | | 2/1997 | Balbierz et al. |
| 5,609,629 A | | 3/1997 | Fearnot et al. |
| 5,647,843 A | | 7/1997 | Mesrobian et al. |
| 5,667,486 A | | 9/1997 | Mikulich et al. |
| 5,669,930 A | | 9/1997 | Igarashi |
| 5,681,274 A | | 10/1997 | Perkins et al. |
| 5,749,826 A | * | 5/1998 | Faulkner ................... 600/29 |
| 5,766,209 A | | 6/1998 | Devonec |
| 5,782,907 A | | 7/1998 | Frantzen et al. |
| 5,795,319 A | | 8/1998 | Ali et al. |
| 5,840,064 A | | 11/1998 | Liprie |
| 5,843,116 A | | 12/1998 | Crocker et al. |
| 5,921,952 A | | 7/1999 | Desmond, III et al. |
| 5,951,514 A | | 9/1999 | Sahota |
| 5,964,744 A | | 10/1999 | Balbierz et al. |
| 5,971,967 A | | 10/1999 | Willard |
| 6,083,198 A | * | 7/2000 | Afzal ................... 604/101.01 |
| 6,120,523 A | | 9/2000 | Crocker et al. |
| 6,214,037 B1 | | 4/2001 | Mitchell et al. |
| 6,221,060 B1 | | 4/2001 | Willard |
| 6,299,598 B1 | * | 10/2001 | Bander ................... 604/101.03 |
| 6,312,465 B1 | | 11/2001 | Griffin et al. |
| 6,409,741 B1 | | 6/2002 | Crocker et al. |
| 6,558,349 B1 | * | 5/2003 | Kirkman ................... 604/104 |
| 2002/0016565 A1 | | 2/2002 | Zadno-Azizi et al. |
| 2005/0165432 A1 | | 7/2005 | Heinrich |
| 2005/0187578 A1 | * | 8/2005 | Rosenberg et al. ........... 606/232 |
| 2007/0106330 A1 | * | 5/2007 | Rosenberg et al. ........... 606/232 |

FOREIGN PATENT DOCUMENTS

| | | |
|---|---|---|
| JP | 57-90150 | 6/1982 |
| JP | 62-20830 | 8/1994 |
| WO | WO 00/51521 | 9/2000 |

OTHER PUBLICATIONS

Cook Urological Product Catalog—Ureteral Sterns, 1987.
Cook Urological Product Brochure—Filiform Ureteral Multi-Length Silicone Stent Sets, 1989.
Cook Urological Product Catalog—Urological Surgical Products, 1990-1991.
Surgitek Product Brochure—Lubri-Flex Ureteral Stent Kit, "The Solution is Perfectly Clear," 1990.
Bard Product Brochure—Introducing the Bard Urinary Diversion Stent, 1984.
Bard Product Brochure—Stents to Satisfy the Urologist: Figure Four Pigtail, Multi-Length or Specific Length, Silicone or Polyurethane-New Injection Stent, 1988.
Bard/angiomed Product Brochure—Puroflex and Urosoft Cross Stent Sets and Schuller Ureterotomy Stent Sets, 1988.
Bard Product Brochure—Introducing the Bard Pediatric Urethral Stent, 1983.
Bard Urological Division Specialty Catalog, 1986.
Bard Product Brochure—Coil Stent with Figure Four End, 1985.
Cook Urological Product Catalog, 1995.
Cabot Medical Surgitek Product Brochure—Products for Stenting.
Circon Surgitek—Premium Ureteral Stent.
Vance Products, Inc. (affiliated with Cook) Product Catalog—Surgical Products.
Vance Products, Inc. (affiliated with Cook) Product Catalog—Surgical Products, May 12, 1979.
Vance Products, Inc. (affiliated with Cook) Product Catalog—Surgical Products for Urology, May 19, 1980.
Vance Products, Inc. (affiliated with Cook) Product Catalog—Surgical Products for Urology, May 8, 1981.
Vance Products, Inc. (affiliated with Cook) Product Catalog—Urological/Surgical Products, 1982-1983.
Vance Products, Inc. (affiliated with Cook) Product Catalog—Urological/Surgical Products, 1983-1984.
Cook Urological Product Catalog—Urological, Surgical and Endourological Products, 1984-1985.
Cook Urological Product Catalog—Ureteral Catheters, 1986.
Cook Urological Product Catalog—Ureteral Catheters, 1992.
Cook Urological Product Catalog—Stent Spectrum, 1996.
Cook Urological Catalog Supplement, May 1998.
Bard Urological Division Product Catalog, 1998.

* cited by examiner

RETAINING STENT

CROSS-REFERENCE TO RELATED APPLICATIONS

This application is a continuation of U.S. patent application Ser. No. 10/400,201, entitled "Retaining Stent," filed Mar. 25, 2003, now U.S. Pat. No. 7,182,745 which is incorporated herein by reference in its entirety.

BACKGROUND

The invention generally relates to medical devices, such as ureteral stents, and related methods.

Fluid sometimes needs to be drained from a body or needs to be passed from one location in the body to another location. For example, urine located in a ureter must be passed from the ureter through the intramural tunnel into the bladder. The passage of urine through the intramural tunnel is sometimes hindered by obstructions in the intramural tunnel or as a result of a constriction within the intramural tunnel. One way to facilitate the passage of urine through the intramural tunnel is to use a medical device that conveys the urine through a lumen of the medical device. Such medical devices include stents and catheters. Some ureteral stents have coiled members located at the distal and proximal ends of the sent that are intended to limit movement of the sent after placement within the body. Existing stents can, when placed within the body of a patient, cause discomfort to the patient or be ineffective in limiting movement of the sent within a body lumen of the patient, especially when the coiled members are located at opposite ends of the sent.

SUMMARY

The present invention relates to a medical device for passing fluid from one location in a body to another location, while also limiting movement of the medical device while located within the body. The medical device can be a ureteral sent.

In general, in one aspect, the invention involves a medical device for use within a body of a patient. The device includes an elongated section that has a first end and a second end. A first retention member is disposed in proximity to the first end, and a second retention member also is disposed in proximity to the first end. The first and second retention members are spaced apart from each other, and the elongated section extends longitudinally away from the second retention member to the second end. The first and second retention members limit longitudinal movement of the elongated section when the medical device is placed within the body of the patient.

Embodiments of this aspect of the invention can include the following features. The elongated section of the device can define a passage extending from the first end to the second end, and the elongated section can define at least one opening in communication with the passage. A first portion of the elongated section that includes the first end can include a first material that has a first durometer value. A second portion of the elongated section that includes the second end can include a second material that has a second durometer value. The first durometer value can be greater than or equal to the second durometer value or, alternatively, the second durometer value can be greater than the first durometer value. The first and second retention members can be an elastic material. An outer diameter of the first end of the elongated section can be larger than an outer diameter of the second end of the elongated section. Alternatively, an outer diameter of the second end can be larger than an outer diameter of the first end. The first and second retention members can be disposed around an outer diameter of the elongated section. At least one of the first and second retention members can have a toroidal, spherical, elliptical, cylindrical or diamond shape. The medical device can be placed within the body by being released from an elongate member (such as a catheter) and into the body.

In general, in another aspect, the invention relates to a method of manufacturing a medical device for use within a body of a patient. The method involves providing an elongated section that has a first end and a second end. The method also involves providing a first retention member and a second retention member. The method further involves disposing the first retention member on the elongated section in proximity to the first end and disposing the second retention member on the elongated section also in proximity to the first end such that the first and second retention members are spaced apart from each other and the elongated section extends longitudinally away from the second retention member to the second end. The first and second retention members are adapted to limit longitudinal movement of the elongated section when the medical device is placed within the body of the patient.

In this method of manufacturing the medical device, the elongated section can define a passage extending from the first end to the second end, and the elongated section can also define at least one opening in communication with the passage.

In general, in yet another aspect, the invention relates to a method of manufacturing a medical device for use within a body of a patient. This method involves providing a mold that has an inner surface that defines an elongated section that has a first end and a second end. The inner surface of the mold also defines a first retention member disposed in proximity to the first end, and a second retention member also disposed in proximity to the first end. The first and second retention members are spaced apart from each other, and the elongated section extends longitudinally away from the second retention member to the second end. The method also involves injecting a fluid plastic into the mold to form the medical device, and removing the medical device from the mold. The first and second retention members are adapted to limit longitudinal movement of the elongated section when the medical device is placed within the body of the patient.

This method of manufacturing the medical device can further include cooling the fluid plastic after it is injected into the mold to solidify the fluid plastic and form the medical device.

In general, in still another aspect, the invention relates to a method of placing a medical device within a body of a patient. The method involves providing a medical device that has an elongated section that has a first end and a second end. The elongated section has a first retention member disposed in proximity to the first end and a second retention member also disposed in proximity to the first end. The first and second retention members are spaced apart from each other and the elongated section extends longitudinally away from the second retention member to the second end. The method also involves providing an elongate member (such as a catheter) and loading the medical device within that member. The elongate member is then placed within the body of the patient, and the medical device is released from the elongate member to place the medical device within the body. The first and second retention members are adapted to limit longitudinal movement of the elongated section when the medical device is placed within the body of the patient.

This method of placing the medical device can further include positioning the first retention member adjacent to a first opening in a body lumen of the patient and positioning the second retention member adjacent to a second opening in the body lumen of the patient.

In general, in another aspect, the invention relates to another method of placing a medical device within a body of a patient. The method involves providing a medical device that has an elongated section that has a first end and a second end. A first retention member is disposed in proximity to the first end and a second retention member also is disposed in proximity to the first end. The first and second retention members are spaced apart from each other and the elongated section extends longitudinally away from the second retention member to the second end. The method also involves positioning the medical device within the body to locate the first retention member adjacent to a first surface of a tissue in the body and the second retention member adjacent to a second surface of the tissue in the body. The first and second retention members are adapted to limit longitudinal movement of the elongated section when the medical device is placed within the body of the patient. In this method of placing the medical device, the first surface of the tissue can oppose the second surface of the tissue.

The foregoing and other objects, aspects, features, and advantages of the invention will become more apparent from the following description and from the claims.

BRIEF DESCRIPTION OF THE DRAWINGS

In the drawings, like reference characters generally refer to corresponding parts throughout the different views. The drawings are not necessarily to scale, emphasis instead generally being placed on illustrating the principles and concepts of the invention.

DETAILED DESCRIPTION

Figure 1A:
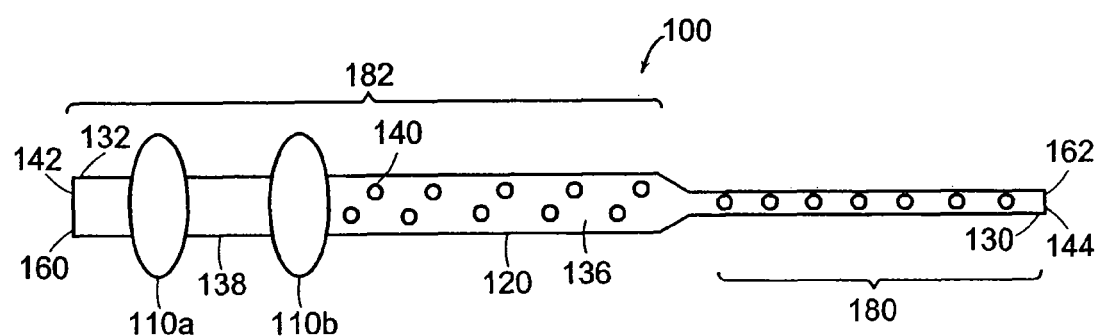
FIG. 1A is a schematic side view of an embodiment of a sent according to the invention.
Figure 1B:
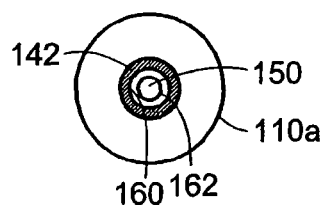
FIG. 1B is a schematic end-on view of the sent of FIG. 1A.

As shown in FIGS. 1A and 1B, one embodiment of a medical device 100 according to the invention includes two retention members 110a and 110b (generally 110) that are disposed on an elongated section 120 of the medical device 100. The retention members 110a and 110b are spaced apart from each other by a first region 138 of the elongated section 120. In this embodiment, the retention members 110a and 110b are toroidal in shape when viewed from the end-on view of FIG. 1B. The retention members 110a and 110b are located in proximity to a first end 132 of the elongated section 120 such that the elongated section 120 extends longitudinally away from the second retention member 110b towards a second end 130 of the elongated section 120. The elongated section 120 has a plurality of openings 140 that allow for fluid communication (and thus fluid to flow) between an outer surface 136 of the elongated section 120 and a lumen 150 defined by the elongated section 120. The lumen 150 is a passage that extends at least partially along the length of the elongated section 120 to facilitate the passage of fluid along at least part of the length of the elongated section 120. The elongated section 120 has an opening 160 located within a first end face 142 of the elongated section 120. The opening 160 is located at the first end 132 of the elongated section 120 and allows fluid to flow out of or into the lumen 150 of the elongated section 120. The elongated section 120 has an additional opening 162 located within a second end face 144 of the elongated section 120. The opening 162 is located at the second end 130 of the elongated section 120 and also allows fluid to flow out of or into the lumen 150 of the elongated section 120.

By way of example, the medical device 100 might be manufactured using a biocompatible material (e.g., thermoplastic resin or polyethylene). The medical device 100 could be manufactured as a unitary body using, for example, an injection molding process in which a fluid plastic (e.g., thermoplastic resin) is injected into a mold. The inside volume of the mold would define an inner surface, and that surface would define locations for and the shape of each of the parts (e.g., the elongated section 120 and the retention members 110a and 110b) of a medical device, such as the medical device 100 of FIGS. 1A and 1B. The fluid plastic would then be permitted to cool sufficiently to yield the medical device 100. The medical device 100 would then be removed from the mold.

Alternatively, the medical device 100 might be manufactured by fusing two flexible plastic retention members 110a and 110b to a plastic elongated section 120 (e.g., by the use of heat) thereby yielding a medical device, such as the medical device 100 of FIGS. 1A and 1B. The retention members 110a and 110b also could be affixed or joined to the elongated section 120 by other means such as by glue. The retention members 110a and 110b can be made of a compressible elastic biocompatible material, for example, such as polyethylene, thermoplastic resin, or silicone. The retention members also can be made of a combination of some or all of these, and/or other, materials.

The entire medical device 100, or parts of it might be formed or fabricated using a flexible elastic material, for example, polyethylene. Alternatively, a first portion 182 of the elongated section 120 that includes the first end 132 might be composed of a first material that has a first durometer value. A second portion 180 of the elongated section 120 that includes the second end 130 might be composed of a second material that has a second durometer value. The first durometer value can be greater than or equal to the second durometer value or, alternatively, the second durometer value can be greater than the first durometer value.

Figure 2:
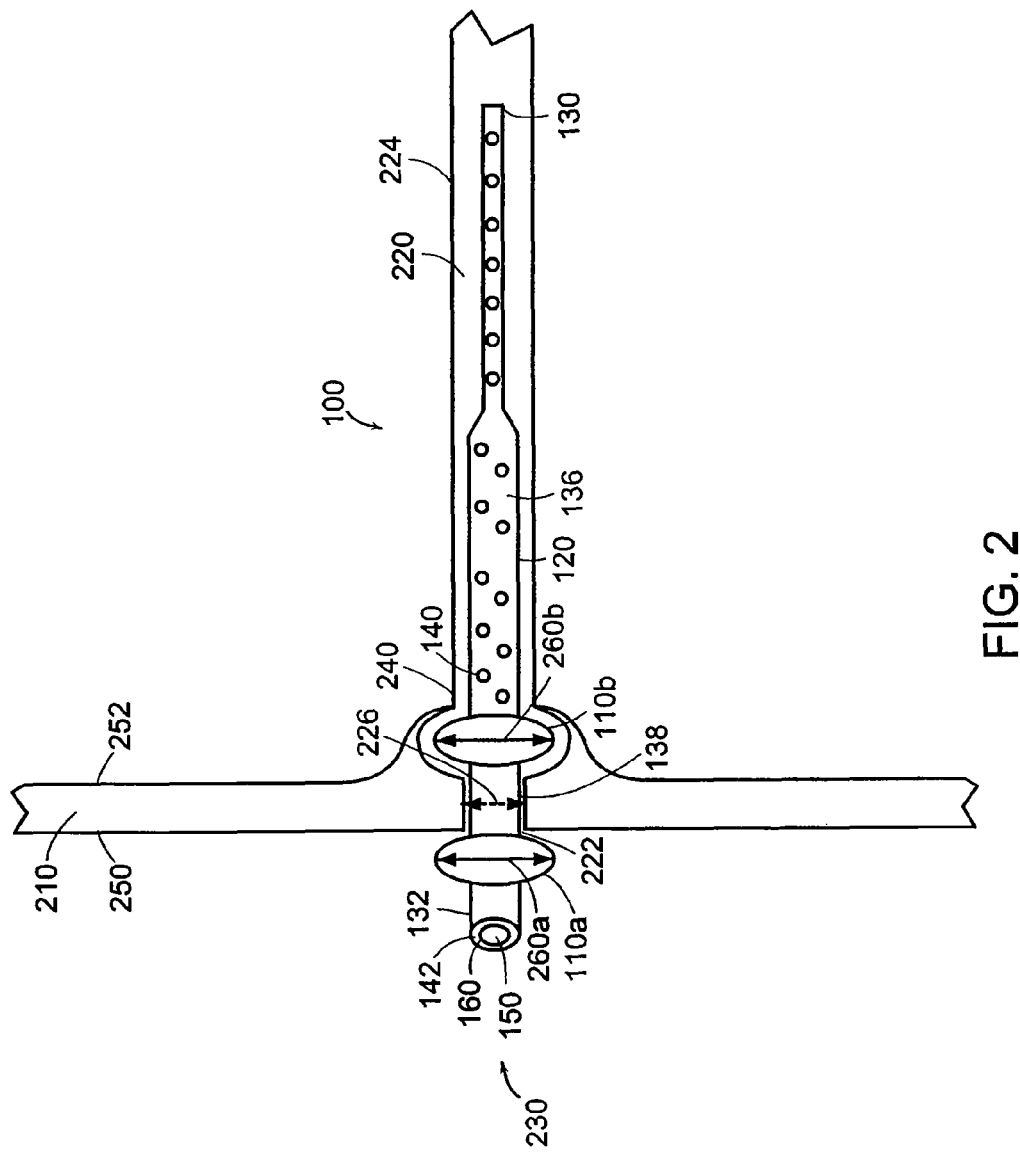
FIG. 2 is an illustration of an embodiment of a sent according to the invention located within a body lumen of a patient.

As shown in FIG. 2, one embodiment of the medical device 100 according to the invention is located within a lumen 220 of a vessel 224 in the body of a patient. A proximal end 240 of the vessel 224 terminates at an opening 222 in a tissue wall 210. The lumen 220 defined by the vessel 224 extends away from the opening 222. Fluid typically passes through the lumen 220 and out of the opening 222 emptying into a region 230 adjacent the opening 222. In this embodiment, the first retention member 110*a* is located in the region 230 and the first retention member 110*a* abuts also a first surface 250 of the tissue wall 210. The second retention member 110*b* is located within the lumen 220 and abuts a second surface 252 of the tissue wall 210. The retention members 110*a* and 110*b* are capable of limiting movement of the elongated section 120 because an outer diameter 260*a* and 260*b* of the retention members 110*a* and 110*b*, respectively, are larger than an inner diameter 226 of the opening 222 in the tissue wall 210. The first region 138 of the elongated section 120 passes through the opening 222 of the tissue wall 210. In this embodiment, fluid in contact with the outer surface 136 of the elongated section 120 may pass through the plurality of openings 140 of the elongated section 120 into the lumen 150 of the elongated section 120. The fluid, subsequently, may pass along the length of the lumen 150 and out of the opening 160 in the elongated section 120.

Figure 3A:
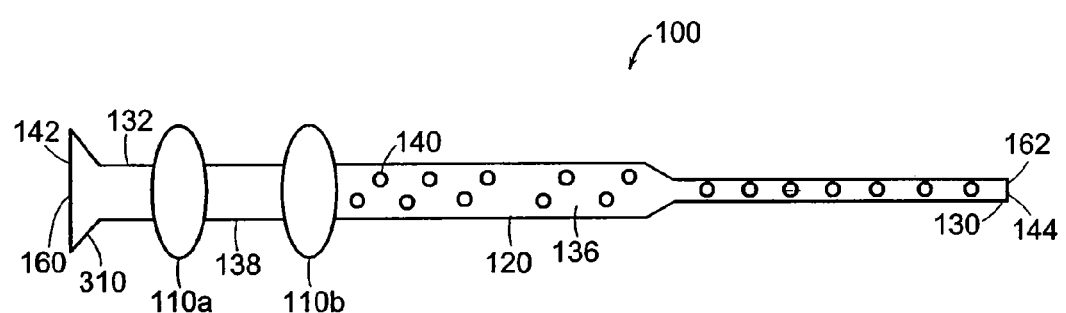
FIG. 3A is a schematic side view of an embodiment of a sent according to the invention.
Figure 3B:
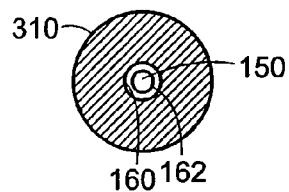
FIG. 3B is a schematic end-on view of the sent of FIG. 3A.

In another embodiment of the invention, as illustrated in FIGS. 3A and 3B, the medical device 100 has a flared section 310 that is located adjacent to the first end 132 of the elongated section 120. The flared section 310 has an opening 160 that permits fluid to flow into or out of the lumen 150 defined by the elongated section 120. The presence of the flared section 310 can facilitate the flow of fluid into the lumen 150 because the flared section 310 has a larger cross-sectional area than does the lumen 150. The lumen 150 permits fluid to flow substantially along the length of and within the elongated section 120. The plurality of openings 140 in the elongated section 120 permit fluid to flow between the outside surface 136 of the elongated section 120 and the lumen 150 of the elongated section 120.

Figure 4A:
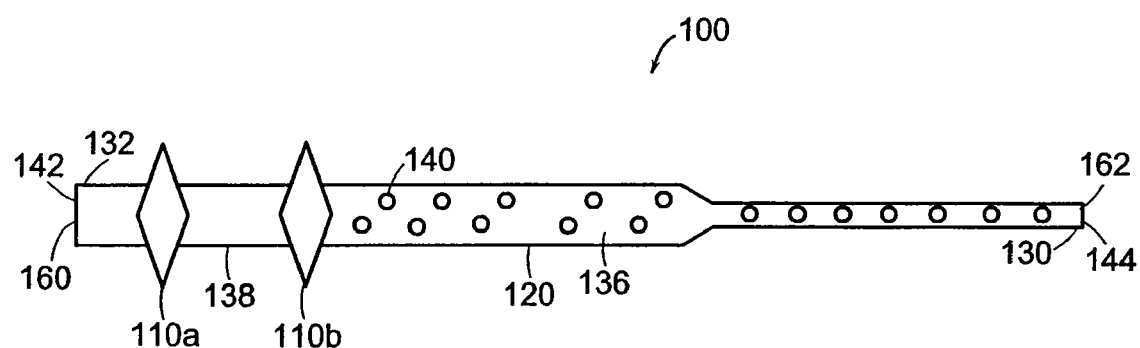
FIG. 4A is a schematic side view of an embodiment of a sent according to the invention.
Figure 4B:
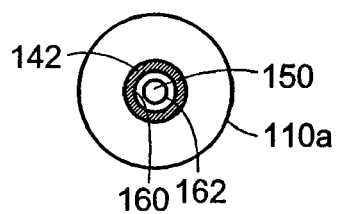
FIG. 4B is a schematic end-on view of the sent of FIG. 4A.

In an alternative embodiment of the invention, as illustrated in FIGS. 4A and 4B, the retention members 110*a* and 110*b* are disposed on or along (by, for example, coupling each of them to) the elongated section 120 of the medical device 100 in proximity to the first end 132 of the elongated section 120. In this embodiment, the retention members 110*a* and 110*b* are diamond-shaped when viewed from the side as shown in FIG. 4A. The shape of each retention member 110*a* and 110*b* could, alternatively, be any geometric shape (e.g., spherical, elliptical, or cylindrical) that is compatible with the placement of the medical device 100 within, for example, the opening in a body lumen of a patient.

Figure 5A:
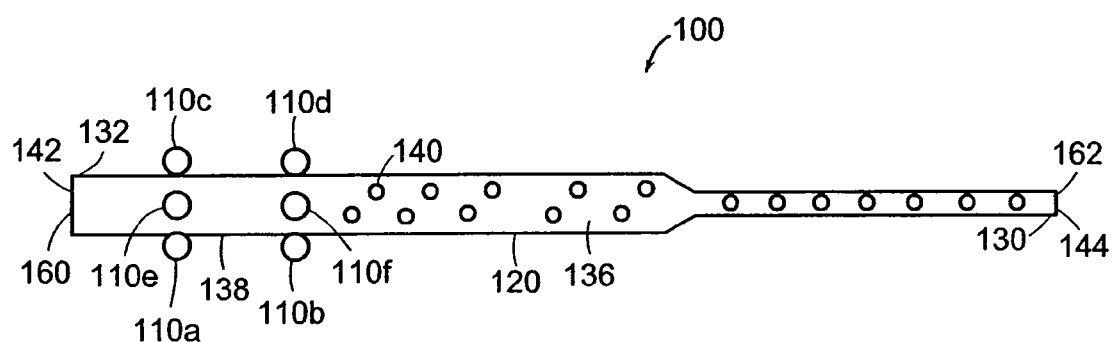
FIG. 5A is a schematic side view of an embodiment of a sent according to the invention.
Figure 5B:
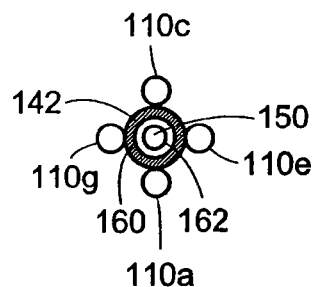
FIG. 5B is a schematic end-on view of the sent of FIG. 5A.

In another embodiment of one aspect of the invention, as illustrated in FIGS. 5A and 5B, eight spherical retention members 110*a* through 110*h* are attached to the elongated section 120. Referring now to FIG. 5A, the retention member 110*h* is located on the opposite side of the elongated section 120 relative to the retention member 110*f* and is not shown for clarity of illustration purposes. The retention members 110*a* through 110*h* are coupled to the first end 132 of the elongated section 120. The retention members 110*a*, 110*c*, 110*e* and 110*g* are located 90 degrees apart from each other and along an outside diameter of the elongated section 120, referring now to FIG. 5B. The retention members 110*b*, 110*d*, 110*f* and 110*h* are spaced apart, by the first region 138, from the retention members 110*a*, 110*c*, 110*e* and 110*g*, respectively.

Figure 6A:
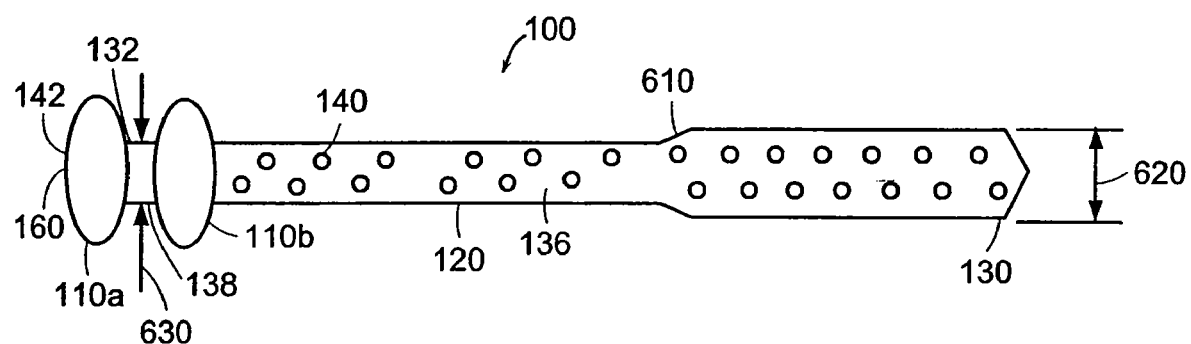
FIG. 6A is a schematic side view of an embodiment of a sent according to the invention.
Figure 6B:
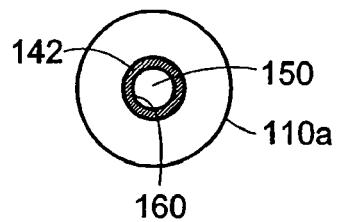
FIG. 6B is a schematic end-on view of the sent of FIG. 6A.

In another embodiment of the invention, as illustrated in FIGS. 6A and 6B, the elongated section 120 has a tapered region 610. The elongated section 120 has a diameter 620 at the second end 130 of the elongated section 120 and a diameter 630 at the first end 132 of the elongated section. In this embodiment, the diameter 620 is larger than the diameter 630. This embodiment of the invention might be used, for example, in an endopyelotomy procedure in which the medical device 100 is inserted into the body of a patient such that the second end 130 of the elongated section 120 is located in a ureter of the patient. Alternatively, in another embodiment, the diameter 620 may be smaller than the diameter 630.

Figure 7A:
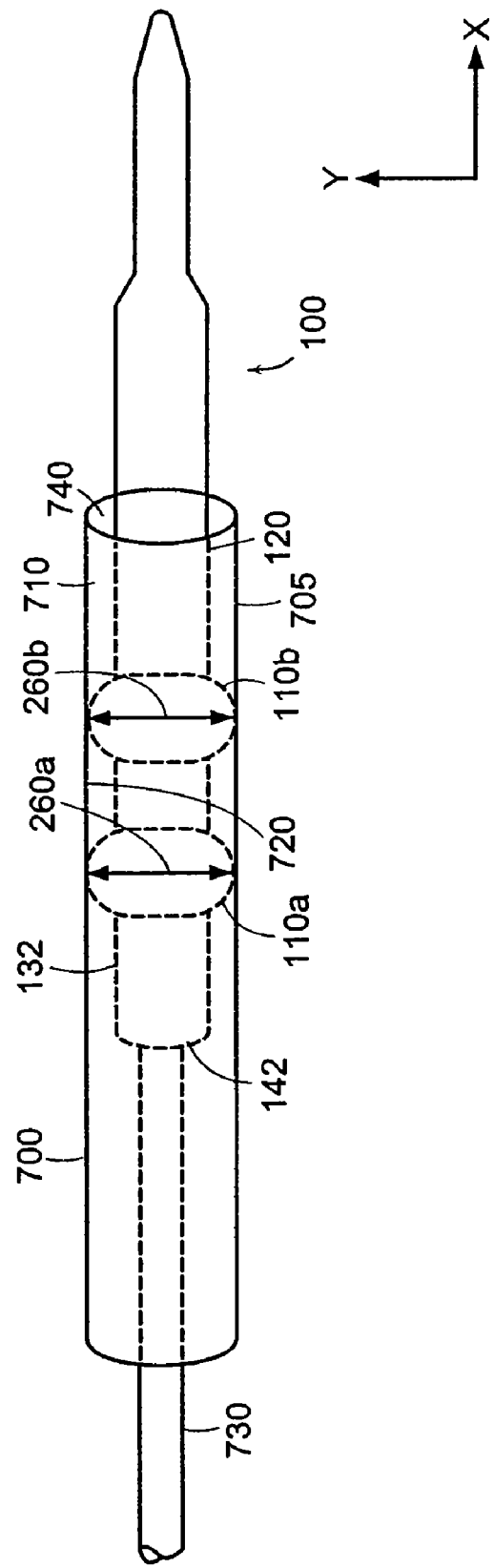
FIG. 7A is an illustration of an embodiment of a sent according to the invention located within a lumen of an elongate member, such as a delivery catheter.
Figure 7B:
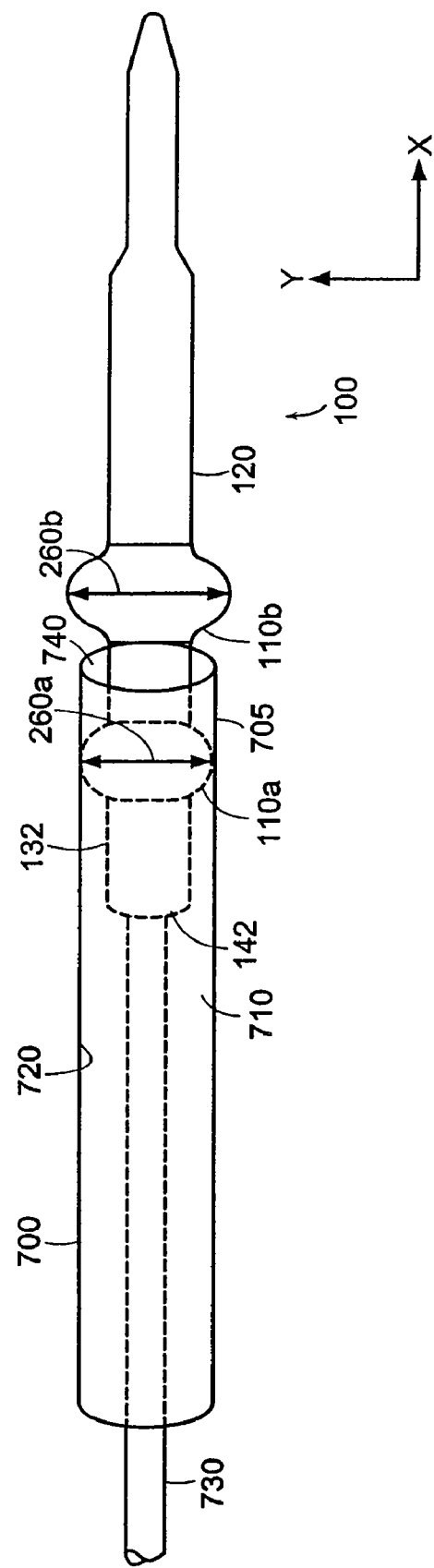
FIG. 7B is an illustration of an embodiment of the sent of FIG. 7A with a retention member being released from an opening in the elongate member.
Figure 7C:
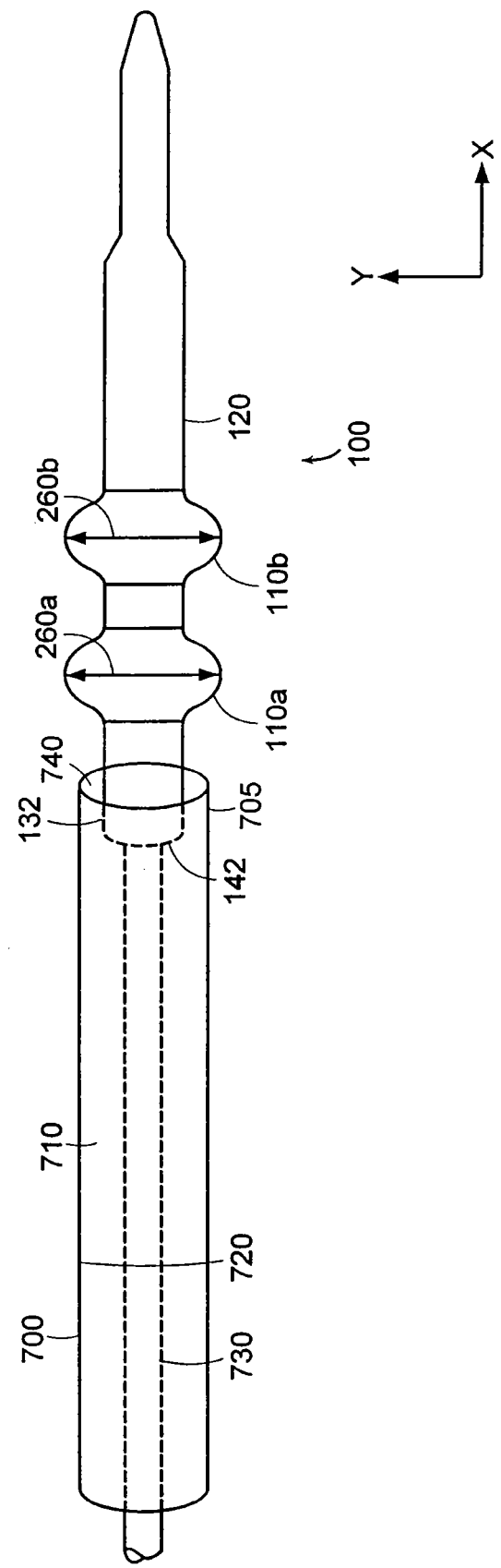
FIG. 7C is an illustration of the sent of FIGS. 7A and 7B with two retention members being released from the opening in the elongate member.

FIGS. 7A, 7B and 7C illustrate steps of an embodiment of the invention, in which the medical device 100 is released from (by, for example, extending it out of) a lumen 710 defined by an elongate member 700. Two retention members 110*a* and 110*b* are located proximal to the first end 132 of the elongated section 120 of the medical device 100. An operator initially compresses the retention members 110*a* and 110*b* so the retention members 110*a* and 110*b* fit within the lumen 710, referring now to FIG. 7A. An inner wall 720 of the elongate member 120 applies a compression force to the retention members 110*a* and 110*b* along the Y-axis when the medical device 100 is located within the lumen 710 of the elongate member 700. A delivery member 730 is coupled to the end face 142 of the elongated section 120. The delivery member 730 is capable of extending and/or retracting the medical device 100 along the X-axis of the lumen 710 of the elongate member 700. Alternatively, the elongate member 700 can be retracted and/or extended along the X-axis relative to the medical device 100 to achieve a similar result.

The delivery member 730 of the invention can be extended in the positive direction along the X-axis such that the retention member 110*b* emerges from an opening 740 at a distal end 705 of the elongate member 700, referring now to FIG. 7B. As the retention member 110*b* emerges from the opening 740 the diameter 260*b* of the retention member 110*b* increases because the inner wall 720 of the elongate member 700 no longer applies a compression force to the retention member 110*b*.

Referring now to FIG. 7C, the delivery member 730 is further extended in the positive direction along the X-axis causing the retention member 110*a* to emerge from the opening 740 of the elongate member 700. The diameter 260*a* of the retention member 110*a* increases as the retention member 110*a* emerges from the opening 740 of the elongate member 700 because the inner wall 720 of the elongate member 700 no longer applies a compression force to the retention member 110*a*.

By way of example, in one embodiment the elongate member 700 is a delivery catheter, for example, a C-Flex® brand catheter manufactured by Boston Scientific Corporation, with offices in Natick, Mass. A medical device, such as the medical device 100 of FIGS. 1A and 1B, can be loaded into a lumen of the catheter and subsequently released from (by, for example, extending it out of) the catheter and placed within a body lumen of a patient. An operator would position the retention members 110*a* and 110*b* such that the retention members 110*a* and 110*b* are located adjacent to first and second openings, respectively, in the body lumen of the patient. The retention members 110a and 110b would, thus, be positioned to limit longitudinal movement of the elongated section 120 of the medical device 100. Alternatively, the elongate member 700 might be a flexible tube manufactured using a biocompatible material, e.g., polyethylene. In general, the elongate member 700 is sufficiently rigid, however, to be capable of applying a compression force to the retention members 110a and 110b when the retention members 110a and 110b are situated within the lumen 710 of the elongate member 700.

FIGS. 8A, 8B, 8C and 8D illustrate steps of an embodiment of the invention, in which the medical device 100 is inserted into an intramural tunnel 812 of a patient, for example, for purposes of facilitating the passage of urine from a kidney 804 through a ureter 808 and, subsequently through the intramural tunnel 812 emptying into a bladder 800. In this embodiment of the invention, the medical device 100 is shown initially as being located within the lumen 710 defined by the elongate member 700, referring now to FIG. 8A, that has been previously introduced into the bladder 800 by an operator. The delivery member 730 is coupled to the first end 132 of the elongated section 120.

Figure 8A:
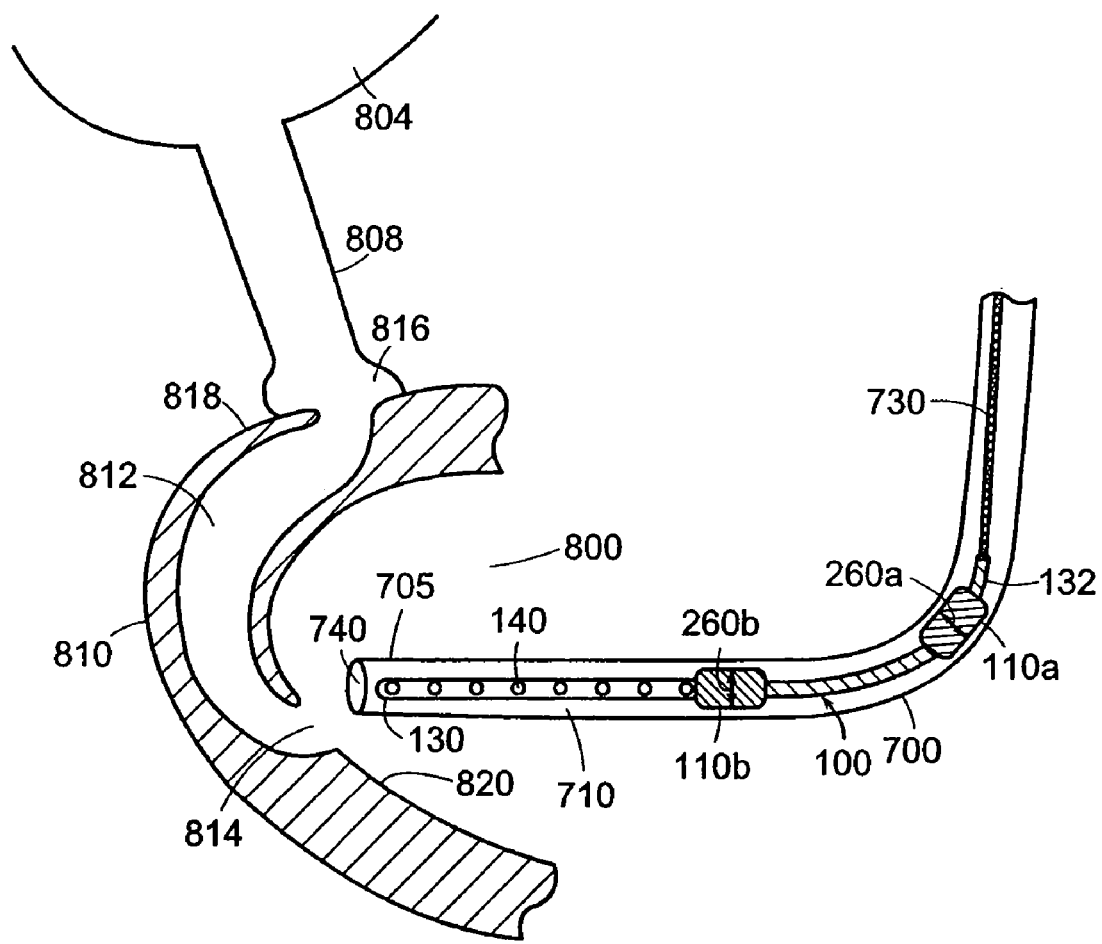
FIG. 8A is a section view of a ureter and bladder of a human body illustrating an embodiment of a sent and elongate member of the invention prior to insertion of the sent and elongate member into the intramural tunnel.
Figure 8B:
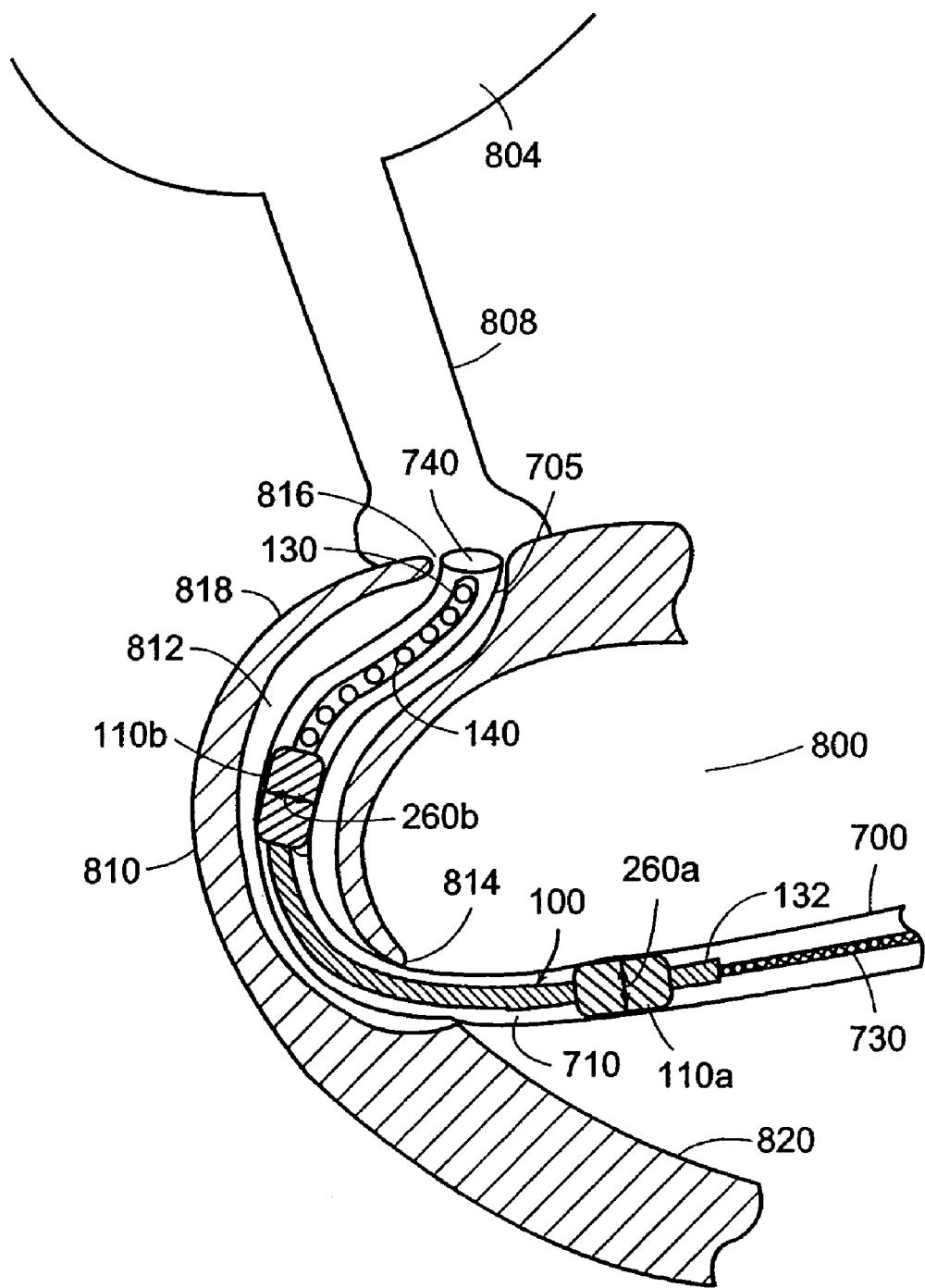
FIG. 8B is a section view of a ureter and bladder of a human body with the sent and elongate member of FIG. 8A located within the intramural tunnel.

Referring now to FIG. 8B, the distal end 705 of the elongate member 700 is inserted into the intramural tunnel 812 through a ureteral orifice 814. The elongate member 700 and medical device 100 located within the elongate member 700 are then advanced through the intramural tunnel 812 towards an opening 816 that is adjacent to the ureter 808. The elongate member 700 and the medical device 100 are advanced until the opening 740 in the distal end 705 of the elongate member 700 has passed beyond the opening 816 in the intramural tunnel 812. The ureter 808 originates at the opening 816 in the intramural tunnel 812 and extends from the opening 816 towards the kidney 804.

Figure 8C:
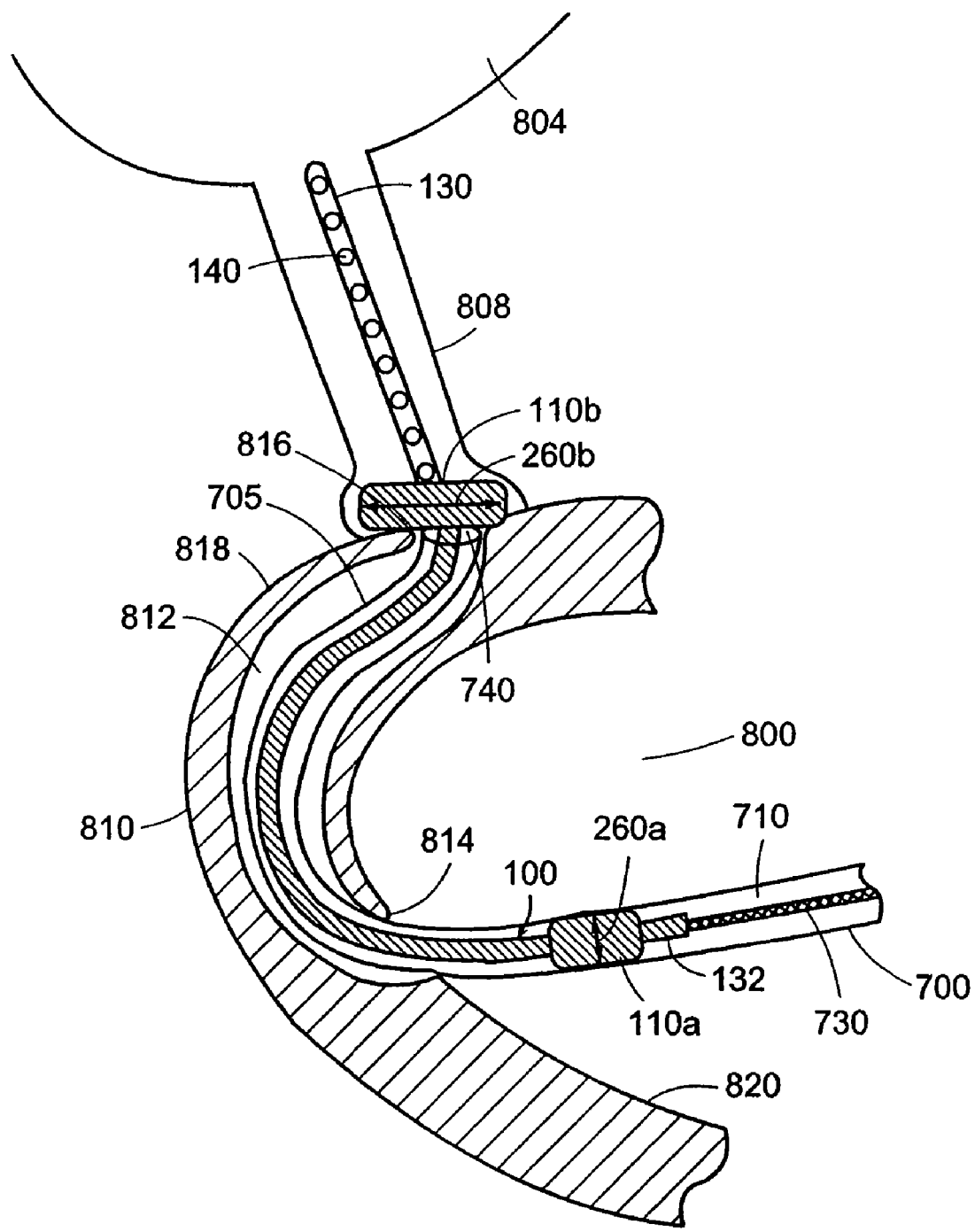
FIG. 8C is a section view of a ureter and bladder of a human body with one retention member of the sent of FIGS. 8A and 8B being released from the elongate member.

The delivery member 730 is then advanced, thereby advancing the medical device 100 along the lumen 710 defined by the elongate member 700, referring now to FIG. 8C. The medical device 100 is advanced until the retention member 110b exits the opening 740 of the distal end 705 of the elongate member 700. The diameter 260b of the retention member 110b increases as it exits the opening 740 as described previously herein. The second end 130 of the medical device 100 is now located partially within the ureter 808 and partially within the kidney 804.

Figure 8D:
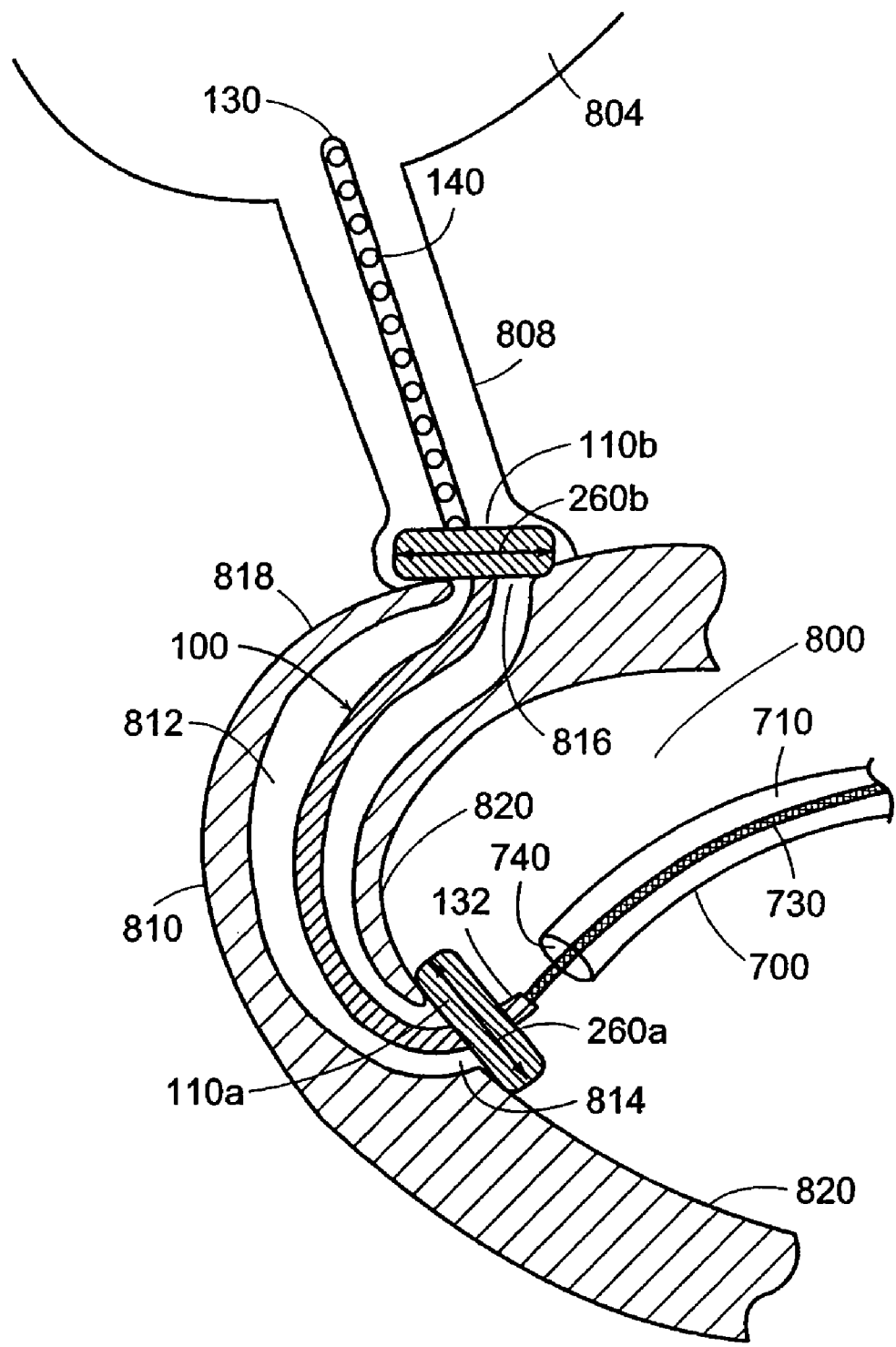
FIG. 8D is a section view of a ureter and bladder of a human body with the sent of FIGS. 8A, 8B and 8C located within the intramural tunnel.

Referring now to FIG. 8D, the elongate member 700 is then retracted proximally with respect to the first end 132 of the elongated section 120 such that the retention member 110a emerges from the opening 740 in the elongate member 700. The retention member 110a also expands in diameter upon emerging from the opening 740 of the elongate member 700 as previously described herein. Upon emerging from the opening 740, the retention member 110a abuts a first surface 820 of a bladder wall 810. The retention member 110b abuts a second surface 818 of the bladder wall 810. The retention members 110a and 110b have therefore, in this configuration, been adapted to limit longitudinal movement of the elongated section 120 when the medical device 100 is placed within the body of the patient.

In general, alternate steps can be used for introducing an embodiment of the medical device 100 of the invention into a body lumen of a patient. For example, a guidewire can first be inserted into the body lumen of the patient. An operator can then place the lumen 150 of the elongated section 120 of the medical device 100 over a free end of the guidewire and subsequently advance the medical device 100 through the body of a patient using an delivery member, such as the delivery member 730 of FIG. 7A. The operator would then utilize the delivery member 730 to position the medical device 100 in a body lumen of the patient such that the retention members 110a and 110b would be positioned to limit movement of the elongated section 120 of the medical device 100.

Alternative embodiments of the invention are contemplated for passing bile from the gall bladder through the bile duct and subsequently through the duodenum and into the small intestine. The retention members, such as the retention members 110a and 110b of FIGS. 1A and 1B, would be located on opposing sides of the duodenum with the papilla of the duodenum located between, for example, the two retention members 110a and 110b.

Variations, modifications, and other implementations of what is described herein will occur to those of ordinary skill without departing from the spirit and the scope of the invention. Accordingly, the invention is not to be defined only by the preceding illustrative description.

What is claimed is:

1. A method, comprising:
    forming an elongated section having a first end portion and a second end portion and defining a lumen through at least a portion of the first end portion;
    coupling a first surface of a first retention member to an outer surface of the first end portion of the elongated section; and
    coupling a second retention member to the outer surface of the first end portion of the elongated section,
    the first retention member having a compressed configuration and an expanded configuration, the first retention member being biased in its expanded configuration, a second surface of the first retention member being a first distance from the first surface of the first retention member when the first retention member is in the compressed configuration, the second surface of the first retention member being a second distance greater than the first distance from the first surface of the first retention member when the first retention member is in the expanded configuration, the second surface of the first retention member being opposite the first surface of the first retention member when the first retention member is in the compressed configuration and when the first retention member is in the expanded configuration,
    the first retention member having a substantially uniform composition along an axis extending radially from the elongate section and intersecting the first surface of the first retention member and the second surface of the first retention member.

2. The method of claim 1, wherein the forming the elongated section includes forming the first end portion from a first material and forming the second end portion from a second material different than the first material.

3. The method of claim 1, wherein the forming the elongated section includes forming the first end portion from a first material, forming the second end portion from a second material different than the first material and coupling the first end portion to the second end portion.

4. The method of claim 1, wherein the forming the elongated section includes forming the first end portion such the first end portion has a diameter and forming the second end portion such the second end portion has a diameter different than the diameter of the first end portion.

5. The method of claim 1, wherein the forming the elongated section includes forming a flared portion disposed adjacent the first end portion, the flared portion defining a lumen therethrough, the lumen of the flared portion being in fluid communication with the lumen of the first end portion, the lumen of the flared portion having a size greater than a size of the lumen of the first end portion.

6. The method of claim 1, wherein the coupling the second retention member includes coupling the second retention member such that the second retention member is spaced apart from the first retention member.

7. The method of claim 1, wherein:
the coupling the first retention member includes coupling the first retention member at a first position on the outer surface of the first end portion; and
the coupling the second retention member includes coupling the second retention member at a second position on the outer surface of the first end portion, the second position being spaced longitudinally apart from the first position.

8. The method of claim 1, wherein:
the coupling the first retention member includes coupling the first retention member at a first position on the outer surface of the first end portion; and
the coupling the second retention member includes coupling the second retention member at a second position on the outer surface of the first end portion, the second position being spaced circumferentially apart from the first position.

9. The method of claim 1, wherein:
the coupling the first retention member includes coupling the first retention member such that the first retention member does not extend longitudinally past an end of the first end portion of the elongated section.

10. The method of claim 1, wherein the coupling the first retention member includes heat bonding the first retention member to the outer surface of the first end portion of the elongated section.

11. The method of claim 1, further comprising:
disposing at least the first retention member within an elongated member such that the first retention member is maintained in the compressed configuration.

12. The method of claim 1, wherein the coupling the first retention member includes coupling the first retention member at a first position on the outer surface of the first end portion, the coupling the second retention member includes coupling the second retention member at a second position on the outer surface of the first end portion, the second position being spaced circumferentially apart from the first position, the method further comprising:
coupling a third retention member to the outer surface of the first end portion of the elongated section at a third position, the third position being spaced circumferentially apart from the first position and the second position.

13. The method of claim 12, wherein:
the second position is spaced circumferentially apart from the first position by approximately ninety degrees; and
the third position is spaced circumferentially apart from the second position by approximately ninety degrees.

14. The method of claim 12, further comprising:
coupling a fourth retention member to the outer surface of the first end portion of the elongated section at a fourth position, the fourth position being spaced circumferentially apart from the first position, the second position and the third position.

15. The method of claim 1, wherein the coupling a first surface of a first retention member includes coupling the first surface of the first retention member to a portion of the outer surface of the elongated section that is devoid of a lumen extending from an interior of the elongated section to the outer surface.

16. The method of claim 1, wherein the coupling a first surface of a first retention member includes coupling the first surface of the first retention member to the outer surface of the elongated section such that an interior of the first retention member is fluidically isolated from an interior of the elongated section.

17. The method of claim 1, wherein the first retention member has a substantially uniform composition between the first surface of the first retention member and the second surface of the retention member.

18. The method of claim 1, wherein the forming includes forming an elongated section that defines a single lumen, an interior of the first retention member being fluidically isolated from the lumen defined by the elongated section.

19. The method of claim 1, wherein the coupling a second surface of the first retention member to an outer surface of the first end portion of the elongated section includes coupling the second surface of the retention member to the outer surface of the end portion of the elongated section such that the outer surface of a portion of the elongated section extending from the first retention member to the second retention member is devoid of openings.

20. A method, comprising:
forming an elongated section having a first end portion and a second end portion and defining a lumen through at least a portion of the first end portion;
coupling a first retention member to an outer surface of the first end portion of the elongated section,
the first retention member having a compressed configuration and an expanded configuration, the first retention member biased in the expanded configuration;
coupling a second retention member to the outer surface of the first end portion of the elongated section; and
disposing at least the first retention member within an elongated member such that the first retention member is maintained in the compressed configuration within the elongated member.

21. The method of claim 20, wherein the first retention member is formed from a compressible elastic material is selected from a group consisting of polyethylene, thermoplastic resin and silicone.

22. The method of claim 20, wherein the first retention member is formed from a substantially homogeneous compressible elastic material.

23. The method of claim 20, wherein the forming the elongated section includes forming the first end portion from a first material and forming the second end portion from a second material different than the first material.

24. The method of claim 20, wherein the forming the elongated section includes forming the first end portion such that the first end portion has a diameter and forming the second end portion such the second end portion has a diameter different than the diameter of the first end portion.

25. The method of claim 20, wherein the coupling the second retention member includes coupling the second retention member such that the second retention member is spaced apart from the first retention member.

26. The method of claim 20, wherein:
the coupling the first retention member includes coupling the first retention member at a first position on the outer surface of the first end portion; and
the coupling the second retention member includes coupling the second retention member at a second position on the outer surface of the first end portion, the second position being spaced longitudinally apart from the first position.

27. The method of claim 20, wherein:
- the coupling the first retention member includes coupling the first retention member at a first position on the outer surface of the first end portion; and
- the coupling the second retention member includes coupling the second retention member at a second position on the outer surface of the first end portion, the second position being spaced circumferentially apart from the first position.

28. The method of claim 20, wherein the coupling the first retention member includes coupling the first retention member at a first position on the outer surface of the first end portion, the coupling the second retention member includes coupling the second retention member at a second position on the outer surface of the first end portion, the second position being spaced circumferentially apart from the first position, the method further comprising:
- coupling a third retention member to the outer surface of the first end portion of the elongated section at a third position, the third position being spaced circumferentially apart from the first position and the second position.

29. The method of claim 28, further comprising:
- coupling a fourth retention member to the outer surface of the first end portion of the elongated section at a fourth position, the fourth position being spaced circumferentially apart from the first position, the second position and the third position.

30. The method of claim 20, wherein the coupling a first retention member to an outer surface includes coupling the first surface of the first retention member to a portion of the outer surface of the elongated section that is devoid of a lumen extending from an interior of the elongated section to the outer surface.

31. The method of claim 20, wherein the coupling a first retention member to an outer surface includes coupling the first surface of the first retention member to the outer surface of the elongated section such that an interior of the first retention member is fluidically isolated from an interior of the elongated section.

32. The method of claim 20, wherein the forming includes forming an elongated section that defines a single lumen, an interior of the first retention member being fluidically isolated from the lumen defined by the elongated section.

33. The method of claim 20, wherein the coupling a second surface of the first retention member to an outer surface of the first end portion of the elongated section includes coupling the second surface of the retention member to the outer surface of the end portion of the elongated section such that the outer surface of a portion of the elongated section extending from the first retention member to the second retention member is devoid of openings.

* * * * *